US009510571B2

(12) United States Patent
Kyogoku et al.

(10) Patent No.: US 9,510,571 B2

(45) Date of Patent: Dec. 6, 2016

(54) TRANSGENIC BIRD EXPRESSING FOREIGN GENE USING ENDOPLASMIC RETICULUM CHAPERONE PROMOTER

(75) Inventors: Kenji Kyogoku, Takasago (JP); Hiroyuki Watanabe, Takasago (JP)

(73) Assignee: KANEKA CORPORATION, Osaka (JP)

( * ) Notice: Subject to any disclaimer, the term of this patent is extended or adjusted under 35 U.S.C. 154(b) by 0 days.

(21) Appl. No.: 14/342,208

(22) PCT Filed: Aug. 27, 2012

(86) PCT No.: PCT/JP2012/071609

§ 371 (c)(1), (2), (4) Date: Apr. 22, 2014

(87) PCT Pub. No.: WO2013/031734

PCT Pub. Date: Mar. 7, 2013

(65) Prior Publication Data

US 2014/0245465 A1 Aug. 28, 2014

(30) Foreign Application Priority Data

Sep. 2, 2011 (JP) ................................ 2011-191926

(51) Int. Cl.

*A01K 67/027* (2006.01)
*C07K 14/505* (2006.01)

(52) U.S. Cl.

CPC ......... *A01K 67/0275* (2013.01); *C07K 14/505* (2013.01); *A01K 2217/052* (2013.01); *A01K 2227/30* (2013.01); *A01K 2267/01* (2013.01); *C12N 2740/13043* (2013.01); *C12N 2830/00* (2013.01); *C12N 2830/90* (2013.01)

(58) Field of Classification Search

USPC ............................................ 800/19, 21, 4, 5
See application file for complete search history.

(56) References Cited

U.S. PATENT DOCUMENTS

| | | | | |
|---|---|---|---|---|
| 2009/0148471 A1* | 6/2009 | Wu | A61K 39/0011 | 424/192.1 |
| 2015/0191713 A1* | 7/2015 | Ciplys | C12P 21/02 | 435/69.8 |

FOREIGN PATENT DOCUMENTS

| | | |
|---|---|---|
| JP | 11-243959 | 9/1999 |
| JP | 2001-054391 | 2/2001 |
| JP | 2004-236626 | 8/2004 |
| JP | 2005-536984 | 12/2005 |
| JP | 2007-089578 | 4/2007 |
| WO | WO 00/29429 | 5/2000 |

OTHER PUBLICATIONS

Table of Bird Classification Families of the Eastern US Birds, 2009.*
Lillico (PNAS, 2007, 104 (5) p. 1771-1776).*
Description of GRP-78, 2015.*
JP2004-236626 translation, 2004.*
"Molecular chaperones of the endoplasmic reticulum," Handbook of Molecular Chaperones (2010), Durante, P. ed., Nova Sci. Publishers, Hauppauge, NY, p. 1-77.*
Byun et al., "Oviduct-Specific Enhanced Green Fluorescent Protein Expression in Transgenic Chickens", Biosci. Biotechnol. Biochem., vol. 75, No. 4 (2011) pp. 646-649.
International Preliminary Report on Patentability issued in International Application No. PCT/JP2012/071609 on Mar. 4, 2014.
Kaleri et al., "Oviduct-specific expression of tissue plasminogen activator in laying hens", Genetics and Molecular Biology, vol. 34, No. 2 (2011) pp. 231-236.
Lillico et al., "Oviduct-specific expression of two therapeutic proteins in transgenic hens", PNAS. vol. 104, No. 6 (2007) pp. 1771-1776.
Wang et al., "Recombinant Avian Adeno-Associated Virus-Mediated Oviduct-Specific Expression of Recombinant Human Tissue Kallikrein", Poultry Science, vol. 87 (2008) pp. 777-782.

* cited by examiner

*Primary Examiner* — Michael Wilson

(74) *Attorney, Agent, or Firm* — Birch, Stewart, Kolasch & Birch, LLP

(57) ABSTRACT

An aim is to produce a suitable foreign protein in egg white in transgenic birds at levels equivalent to or higher than the expression levels achieved using an ovalbumin promoter or an actin promoter, and to reduce the great burden on birds by reducing the expression at sites other than the oviduct while achieving expression sufficient to predict the expression levels before the birds reach sexual maturity. Provided is a transgenic bird containing a nucleic acid base sequence in chromosome in a cell that forms the oviduct, the sequence containing: (a) an avian endoplasmic reticulum chaperone promoter; and (b) a nucleic acid base sequence encoding a suitable foreign protein, functionally linked to the promoter. Also provided is a method for producing a suitable foreign protein, including recovering the suitable foreign protein from the transgenic bird. Further provided is a method for producing a transgenic bird, including introducing a nucleic acid base sequence into a chromosome in a cell that forms the oviduct, the sequence containing: (a) an avian endoplasmic reticulum chaperone promoter; and (b) a nucleic acid base sequence encoding a suitable foreign protein, functionally linked to the promoter.

9 Claims, No Drawings

TRANSGENIC BIRD EXPRESSING FOREIGN GENE USING ENDOPLASMIC RETICULUM CHAPERONE PROMOTER

REFERENCE TO SEQUENCE LISTING SUBMITTED VIA EFS-WEB

This application includes an electronically submitted sequence listing in .txt format. The .txt file contains a sequence listing entitled "2016-04-28 5051-0304PUS1_ST25.txt" created on Apr. 28, 2016 and is 10,593 bytes in size. The sequence listing contained in this .txt file is part of the specification and is hereby incorporated by reference herein in its entirety.

TECHNICAL FIELD

The present invention is relates to transgenic birds, a method for producing a suitable foreign protein, and a method for producing transgenic birds.

BACKGROUND ART

A recent trend in studies on pharmaceutical protein production is the increasing use of transgenic animals. Some attempts were made to accumulate suitable foreign proteins in goats' or sheep's milk. These techniques are already in practical use. The disadvantages of using mammals, such as goats and sheep, are: a large rearing space; a long period to sexual maturity; and a long time-scale for setting up a production line. Alternatively, birds, such as chickens, have been used in an attempt to accumulate a suitable foreign protein in their egg white. Chickens are useful because a large rearing space is not required; hens begin to lay eggs at only about 6 months of age; and their safety is confirmed from our long history of diets. In order to accumulate a suitable foreign protein in egg white, a site-specific promoter for an egg white-localized protein, such as an ovalbumin promoter (Patent Literature 1) or an ovomucoid promoter (Patent Literature 2), is usually used. Or, an actin promoter that allows a protein to be systemically expressed can also be used (Patent Literature 3).

Promoters for proteins that are accumulated in egg white naturally induce oviduct-specific gene expression. Accordingly, they are very useful promoters for accumulation of suitable foreign proteins in egg white. Unfortunately, when they are used in a recombinant DNA technique to express suitable foreign proteins in egg white, their oviduct-specific expression does not allow us to quantify the expression of the suitable foreign proteins until hens lay eggs. It is noted that these promoters do not allow quantification of the expression of suitable foreign proteins, for example, in blood samples from sites other than the oviduct (Non Patent Literature 1, FIG. 3). This means that the productivity of hens as biofactories cannot be checked until hens reach sexual maturity, and that all transgenic hens should be reared until they reach sexual maturity. Effort and costs for rearing low-productive hens until their sexual maturity are serious problems.

By contrast, in the case of using an actin promoter, which allows a target protein to be expressed in the cells throughout the chicken's body, it is possible to predict the amount of protein to be produced to some extent by measuring the concentration of the protein in blood. This enables selection of individuals with high expression before they reach sexual maturity. Unfortunately, some suitable foreign proteins or their physiological functions can be a great burden on chickens when the proteins are systemically expressed. Great burdens on chickens are known and include a decreasing hatching rate, a decreasing survival of hatched individuals, a decreasing reproductive capacity, and a decreasing egg laying ability. Such effects on the chicken's health are expected to greatly affect the production costs.

CITATION LIST

Patent Literature

Patent Literature 1: JP 2004-236626 A

Patent Literature 2: JP 2005-536984 T

Patent Literature 3: JP 2007-89578 A

Non Patent Literature

Non Patent Literature 1: Proc. Natl. Acad. Sci. USA; 104, 2007, 1771-1776

SUMMARY OF INVENTION

Technical Problem

The production of proteins in transgenic birds has the following disadvantages: oviduct-specific expression of proteins does not allow prediction of the amount of proteins to be expressed in the egg white before the birds reach sexual maturity, and accordingly all individuals, including low-productive individuals, should be reared until they reach sexual maturity. The use of actin promoters can be a great burden on chickens because of systemic expression of suitable foreign proteins at high levels, and accordingly, some may require medical treatment and some may die. Costs attributed to these disadvantages are a serious problem for protein production. To overcome these disadvantages, the present invention aims to produce a suitable foreign protein in egg white of transgenic birds at levels equivalent to or higher than the expression levels achieved by the use of an ovalbumin promoter or an actin promoter, and at the same time to reduce the great burden on birds by reducing the expression at sites other than the oviduct while achieving expression sufficient to predict the expression levels before the birds reach sexual maturity.

Solution to Problem

The present inventors found that promoters for endoplasmic reticulum chaperone proteins enable a suitable foreign protein to be expressed in a bird's egg white, specifically to be expressed in a bird's egg white at levels equivalent to or higher than the expression levels achieved by the use of an ovalbumin promoter or an actin promoter, and to reduce the expression at sites other than the oviduct while achieving expression sufficient to predict the expression levels in egg white before they reach sexual maturity, and thus reduce the great burden on birds. Thus, the present invention was completed.

Specifically, the present invention relates to a transgenic bird containing a nucleic acid base sequence in a chromosome in a cell that forms the oviduct, the nucleic acid base sequence containing:

(a) an avian endoplasmic reticulum chaperone promoter; and (b) a nucleic acid base sequence encoding a suitable foreign protein, functionally linked to the promoter (a). Preferably, the endoplasmic reticulum chaperone promoter is from a chicken. The promoter more preferably contains an ER stress response element motif, and is still more preferably a glucose-regulated protein 78 promoter or a protein disulfide isomerase promoter. Preferably, the host is a poultry animal, and more preferably a chicken. The suitable foreign protein is preferably a feline-derived protein.

The present invention also relates to a method for producing a suitable foreign protein, which includes the step of recovering the suitable foreign protein from the transgenic bird.

The present invention further relates to a method for producing a transgenic bird, which includes the step of introducing a nucleic acid base sequence into a chromosome in a cell that forms the oviduct, the nucleic acid base sequence containing: (a) an avian endoplasmic reticulum chaperone promoter; and (b) a nucleic acid base sequence encoding a suitable foreign protein, functionally linked to the promoter (a). The production method preferably further includes the step of sorting the transgenic bird based on expression levels of the suitable foreign protein in blood before sexual maturity. Preferably, the host is a poultry animal, and more preferably a chicken.

Advantageous Effects of Invention

The use of an endoplasmic reticulum chaperone promoter for the expression of a transferred gene encoding a suitable protein allows prediction of the expression levels in transgenic birds of the present invention before they begin to lay eggs, reduces the systemic expression to lower levels, and allows the transgenic birds of the present invention to accumulate the suitable foreign protein in egg white to levels equivalent to the levels that can be achieved by the use of an ovalbumin promoter or an actin promoter.

DESCRIPTION OF EMBODIMENTS

The transgenic birds of the present invention contain a nucleic acid base sequence in a chromosome in a cell that forms the oviduct, the nucleic acid base sequence containing: (a) an avian endoplasmic reticulum chaperone promoter; and (b) a nucleic acid base sequence encoding a suitable foreign protein, functionally linked to the promoter (a).

Any birds can be used as hosts for the transgenic birds without limitation. Preferably, a poultry animal utilizable as a farm animal is used. Examples of poultry animals include chickens, quails, turkeys, ducks, ostriches, and domestic ducks. Chickens and quails are particularly preferable because they are easily available; they are fecund oviparous species; their eggs are large; and mass rearing techniques for them have been established. Among them, chickens are most preferable.

The transgenic birds include G0 transgenic chimeric birds, G1 transgenic birds, and transgenic birds of G2 or later generations.

The endoplasmic reticulum chaperone promoter may be any promoter sequence that is capable of allowing an endoplasmic reticulum chaperone protein to be expressed. Preferred is an avian endoplasmic reticulum chaperone promoter, more preferred is a host-derived endoplasmic reticulum chaperone promoter, and most preferred is a chicken-derived endoplasmic reticulum chaperone promoter.

The endoplasmic reticulum is a type of organelle in the cells of eukaryotic organisms, which synthesizes most of the secretory proteins and membrane proteins. The important role of this organelle is to fold synthesized proteins. The endoplasmic reticulum contains chaperones involved in folding of these secretory proteins and membrane proteins. Examples of endoplasmic reticulum chaperone proteins include Glucose-Regulated Protein 78 (GRP 78/BiP) and protein disulfide isomerase (PDI).

GRP 78 plays a primary role in protein transport through the endoplasmic reticulum and endoplasmic reticulum quality control mechanisms. One of its functions is to bind to newly synthesized proteins as a chaperone to prevent the proteins from aggregating and to accelerate the folding of the proteins.

PDI is an oxidoreductase present in the endoplasmic reticulum. This enzyme catalyzes the formation and rearrangement of disulfide bonds in proteins as they fold. This enzyme has a role as a chaperone to assemble not only modified proteins with non-natural disulfide bonds but also proteins without disulfide bonds into their higher-order structures. PDI is reported to be highly expressed in organs, including liver, thyroid, and stomach, but to be lowly expressed in muscle and heart in experiments with rats (J. Histochemistry and Cytochemistry, 1996, 44, 751). This report does not describe or suggest that endoplasmic reticulum chaperone proteins are expressed in avian oviduct cells that produce egg white proteins. As described above, the endoplasmic reticulum chaperones play key roles in the cells.

Promoters for the endoplasmic reticulum chaperones GRP 78 and PDI contain a motif called ERSE (ER stress response element). The term "promoter" herein refers to a region of DNA that defines a starting point of the transcription of a particular gene, and directly controls the level of the transcription. The promoters contain enhancers that enhance the levels of transcription from the promoters. The ERSE motif contains a sequence consisting of any 9 bases between the sequences CCAAT and CCACG, and thus is represented by CCAATN$_9$CCACG (SEQ ID NO: 7). This sequence is believed to be an important motif for these promoters because alteration of even one base reduces the transcription activities (J. Biological Chemistry, 1998, 273, 33741). In addition to the above-mentioned two endoplasmic reticulum chaperone promoters, calreticulin is also mentioned as an example of endoplasmic reticulum chaperone promoters known to contain an ERSE motif. As is known to those skilled in the art, endoplasmic reticulum chaperone promoters containing an ERSE motif can function similarly to GRP 78 and PDI.

The endoplasmic reticulum chaperone promoter for GRP 78 may be a sequence included in a base sequence amplified by PCR with primers respectively having the base sequences of SEQ ID Nos:3 and 4 in the sequence listing and the genome of a white leghorn chicken as a template. Specifically, the base sequence of SEQ ID No:1 in the sequence listing may be mentioned, for example.

The endoplasmic reticulum chaperone promoter for PDI may be a sequence included in a base sequence amplified by PCR with primers respectively having the base sequences of SEQ ID Nos:5 and 6 in the sequence listing and the genome of a white leghorn chicken as a template. Specifically, the base sequence of SEQ ID No:2 in the sequence listing may be mentioned, for example.

The avian endoplasmic reticulum chaperone promoter may be a DNA capable of hybridizing with a DNA complementary to the DNA of SEQ ID No:1 or 2 in the sequence listing under stringent conditions.

Or, the avian endoplasmic reticulum chaperone promoter may be a DNA having at least 85% sequence identity to the base sequence of SEQ ID No:1 or 2 in the sequence listing.

The phrase "DNA capable of hybridizing with a DNA complementary to the DNA of SEQ ID No:1 or 2 in the sequence listing under stringent conditions" refers to DNAs obtainable by techniques, such as colony hybridization, plaque hybridization and southern hybridization, under stringent conditions using a DNA having a base sequence complementary to the base sequence of SEQ ID NO:1 or 2 in the sequence listing as a probe.

The hybridization can be accomplished according to, for example, the method disclosed in Molecular Cloning, A laboratory manual, second edition (Cold Spring Harbor Laboratory Press, 1989). The phrase "DNA capable of hybridizing under stringent conditions" refers to DNAs obtainable by, for example, hybridization using a filter with a colony- or plaque-derived DNA immobilized thereon in the presence of 0.7 to 1.0 M NaCl at 65° C., and washing of the filter at 65° C. with a 2×SSC solution (the composition of a 1×SSC solution is as follows: 150 mM sodium chloride; and 15 mM sodium citrate). Preferred are DNAs obtainable by washing at 65° C. with a 0.5×SSC solution, more preferred are DNAs obtainable by washing at 65° C. with a 0.2×SSC solution, and still more preferred are DNAs obtainable by washing at 65° C. with a 0.1×SSC solution.

The hybridization conditions are not limited to those described above. Several factors, such as temperature and salt concentration, are thought to influence the stringency of hybridization, and those skilled in the art can select appropriate conditions for the respective factors to achieve the optimal stringency.

As DNAs hybridizable under the above-mentioned conditions, mention may be made of DNAs having at least 70%, preferably at least 85%, more preferably at least 90%, still preferably at least 95%, and most preferably at least 98% sequence identity to the DNA of SEQ ID NO:1 or 2.

The term "sequence identity (%)" as used herein refers to a value determined by optimally aligning two DNAs to be compared, dividing the number of positions at which the identical nucleic acid base (e.g., A, T, C, G, U, or I) occurs in both sequences by the total number of bases compared, and multiplying the result by 100.

For example, the following tools for sequence analysis can be used to calculate the sequence identity:

GCG Wisconsin Package (Program Manual for The Wisconsin Package, Version 8, September, 1994, Genetics Computer Group, 575 Science Drive Medison, Wis., USA 53711;

Rice, P. (1996) Program Manual for EGCG Package, Peter Rice, The Sanger Centre, Hinxton Hall, Cambridge, CB10 1RQ, England); and the ExPASy World Wide Web molecular biology server (Geneva University Hospital and University of Geneva, Geneva, Switzerland).

The suitable foreign protein is not limited at all, and may be a secretory protein, or a protein suitable for the protein industry, such as an antibody, a physiologically active protein, or an enzyme. Examples include secretory proteins, such as erythropoietin, G-CSF, thrombopoietin, and interferons; and artificial antibodies, such as human monoclonal antibodies, chimeric antibodies, and modified antibodies that are made single-stranded. The origin of the protein may be, for example, a farm animal, a poultry animal, a pet, or an experimental animal. Examples of farm animals include cattle, horses, swine, goats, sheep, boar, wild boar/domestic pig hybrid, reindeer, deer, camels, donkeys, mules, rabbits, minks, alpacas, buffaloes, and yaks. Examples of poultry animals include chickens, domestic ducks, geese, ostriches, quails, turkeys, pigeons, and pheasants. Examples of pets include dogs, cats, rabbits, guinea pigs, rats, mice, hamsters, ferrets, parakeets, parrots, foxes, raccoon dogs, monkeys, hill myna, society fintches, Java sparrows, and pigeons. Examples of experimental animals include rats, mice, rabbits, dogs, cats, swine, guinea pigs, monkeys, marmosets, Mongolian gerbils, ferrets, cattle, goats, sheep, chickens, and quails. A specific example of the suitable foreign protein is feline-derived erythropoietin.

In addition to proteins from individuals other than individuals to be engineered into transgenic birds, native proteins from individuals to be engineered into transgenic birds are also included in the scope of the suitable foreign protein because they also need a process of introducing additional base sequences into the original genomes of the individuals.

In order to allow the suitable foreign protein to be expressed, it is preferable that the nucleic acid base sequence encoding the suitable foreign protein be functionally linked downstream of the promoter. The term "functionally linked" means that regulatory elements of the promoter for regulating the expression of the gene and the nucleic acid base sequence encoding the protein are linked to be able to operate in host cells. The boundaries of the coding sequence for the suitable foreign protein to be expressed are defined by a start codon at the 5' end and a corresponding stop codon at the 3' end. The base sequence preferably contains the Kozak consensus sequence near the start codon at the 5' end.

G1 transgenic birds and transgenic birds of G2 and later generations, among the transgenic birds, have a chromosome with the nucleic acid base sequence in which the avian endoplasmic reticulum chaperone promoter and the nucleic acid base sequence encoding the suitable foreign protein are functionally linked, in the cells throughout the body.

By contrast, G0 transgenic chimeric birds, among the transgenic birds, have a chromosome with the nucleic acid base sequence only in part of the cells that make up the oviduct and part of the cells throughout the body. This allows the suitable foreign protein to be accumulated in eggs of the transgenic birds and to be expressed at a detectable level in blood.

The present invention also relates to a method for producing a transgenic bird, which includes the step of introducing a nucleic acid base sequence into a chromosome in a cell that forms the oviduct, the nucleic acid base sequence containing the avian endoplasmic reticulum chaperone promoter and the nucleic acid base sequence encoding the suitable foreign protein, functionally linked to the promoter.

In the step of introducing a foreign gene into a chromosome to produce transgenic birds, a retroviral vector is preferably used. The term "retroviral vector" is intended to include vectors of different forms, such as plasmids, virus particles, and packaging cells. Packaging cells are cells in which a gene encoding at least one protein necessary for replication of virus particles is introduced.

For safety reasons, a replication defective retroviral vector is preferably used for the production of transgenic birds. Preferably, the retroviral vector is rendered replication defective by at least partially or completely deleting the sequences encoding the following proteins necessary for replication of virus particles: the protein in the internal core (group specific antigen, gag); reverse transcriptase (polymerase, pol); and envelope glycoprotein (envelope, env), or by at least partially or completely deleting sequences necessary for the expression of these sequences so that any one or a combination of these proteins is not expressed. Alternatively, the retroviral vector preferably contains substitution(s) and/or insertion(s) so that these proteins are not expressed. Since the acceptable gene length is limited depending on the viral species, the retroviral vector preferably contains a deletion. In order to ensure safety and increase the insert fragment length, the retroviral vector preferably contains a mutation that makes the vector incapable of reproducing gag, pol and/or env. Preferably, the retroviral vector contains a viral packaging signal (phi), which functions as a signal for packaging of the vector in a virus particle. Since part of the gag region may function as a viral packaging signal, the viral vector preferably contains at least part of the gag region which is rendered incapable of being expressed, in order to increase the virus titer (J. Virol., 1987, 61(5), 1639).

Any retrovirus can be used without limitation. For example, mention may be made of viruses derived from Moloney murine leukemia virus, Moloney murine sarcoma virus, avian leukemia virus (ALV), and human immunodeficiency virus (HIV). Viruses highly capable of infecting germ cells and stem cells, such as murine stem cell virus and murine embryonic stem cell virus (MSCV), are preferably used for the infection of avian embryos. MSCV is more preferable. The replication defective retroviral vector preferably contains a sequence derived from any of these viruses. For effective infection of avian cells with such a viral vector, it is preferable to artificially replace the coat protein with the bovine vesicular stomatitis virus-derived VSV-G envelope protein. It should be noted that the envelope protein is not limited to viruses of this type.

The replication defective retroviral vector may contain a transcriptional enhancer and/or regulatory element(s). The term "transcription enhancer" means a sequence that enhances the level of transcription from a promoter sequence, and is unable to initiate transcription by itself. Examples of the enhancer include, but not particularly limited to, enhancers of simian virus 40 (SV40), cytomegalovirus (CMV), thymidine kinase, steroid responsive elements, and lysozymes. The term "regulatory element" means a sequence which contributes to transcriptional regulation and stabilization of transcribed RNA, and is unable to initiate transcription by itself. Examples of regulatory elements include, but not limited to, WPRE (woodchuck hepatitis virus posttranscriptional regulatory element, U.S. Pat. No. 6,136,597).

The retroviral vector contains at least a part of a long terminal repeat (LTR) at both the 5' and 3' ends. LTRs can be used as promoter and/or terminator genes because they contain a transcription promoter gene and a polyadenylation signal. Preferably, the nucleic acid sequence of the retroviral vector is designed such that the coding gene for the suitable foreign protein, the promoter, and the transcription enhancer and/or regulatory element(s) are present between 5'LTR and 3'LTR, and that the gene for the suitable foreign protein is functionally linked downstream of the promoter. The phrase "functionally linked" means that the gene and regulatory elements of the promoter for regulating the expression of the gene are linked to be able to operate in host cells. As known to those skilled in the art, the type and kind of regulators depend on the host.

In order to ensure that the retroviral vector is transcribed to form virus particles, the sequence preferably contains no terminator and no polyadenylation signal between 5'LTR and 3'LTR.

The retroviral vector may contain a marker gene. The marker gene is a gene encoding a protein that serves as a marker for identifying and isolating cells in which a particular gene is successfully introduced. Examples of the marker gene include, but not particularly limited to, genes coding fluorescence proteins such as green fluorescent protein (GFP), cyan fluorescent protein (CFP), and luciferase; drug resistance genes such as neomycin resistance gene ($Neo^r$), hygromycin resistance gene ($Hyg^r$), and puromycin resistance gene ($Puro^r$), and genes encoding thymidine kinase and β-galactosidase. The marker gene is preferably accompanied by a general promoter sequence and/or other elements necessary for the expression thereof.

The replication defective retroviral vector lacks the gag, pol, and/or env genes, which are necessary for replication. The replication defective retroviral vector can be prepared as follows: simultaneously introducing a replication defective retroviral plasmid capable of expressing the target protein and a VSV-G expression plasmid into a packaging cell containing the gag and pol genes; and culturing the cell to recover the culture supernatant as a virus solution. Preferably, the above-mentioned virus solution is used to infect a packaging cell, a VSV-G expression plasmid is introduced into the cell, and the cell is cultured to recover the culture supernatant as a virus solution. The method for obtaining a virus solution is not limited to these.

The titer of the replication defective retroviral vector in the virus solution is not particularly limited as long as the solution has infection ability. The titer, when determined after centrifugation enrichment, is preferably $1\times10^8$ to $1\times10^{14}$ cfu/ml, and more preferably $1\times10^9$ to $1\times10^{14}$ cfu/ml.

The titer of the virus solution is determined by adding the virus solution to NIH3T3 cells (American Type Culture Collection CRL-1658), and counting infected cells. Specifically, the titer of the virus solution is determined as follows: diluting a 1 μl portion of the virus solution in 2 ml of a medium; further diluting this dilution to concentrations of $10^1$ to $10^5$; charging the resulting dilutions to 6-well culture plates, each well of which contains $1.5\times10^4$ NIH3T3 cells; and determining the proportion of cells expressing the neomycin resistance gene, which is a marker gene, based on the resistance against G418.

The transgenic birds can be suitably produced by a method involving infecting avian embryos with the replication defective retroviral vector containing the promoter and the foreign gene, and hatching the embryos. The term "embryo" refers to a multicellular organism in its earliest stage of development which is enveloped in a chorion or eggshell or is in the mother's body, and does not yet take food independently. The term "hatching" means coming out of the chorion or eggshell and beginning to take food independently.

Any avian embryos can be used for the infection with the replication defective retroviral vector without limitation. Preferably, avian embryos after at least 24 hours from the start of incubation are used. Avian embryos 32 hours to 72 hours after the start of incubation are more preferable, and avian embryos 48 hours to 64 hours after the start of incubation are still more preferable. The virus infection site, namely the site into which the virus solution is injected is not limited at all, and injection into the heart or into a blood vessel is preferable. For the purpose of producing G0 transgenic chimeric birds with high gene transfer efficiency, the gene transfer is preferably carried out at the early stage at which the cardiac pulsation can be observed. The stage is, for example, within 6 hours after the start of cardiac pulsation. This is concluded from the facts that the gene is to be distributed throughout the body by means of blood circulation, and that embryos have fewer cells.

The term "incubation" means fertilized avian eggs immediately after being laid or fertilized avian eggs stored, immediately after being laid, in an environment in which embryogenesis does not occur are maintained in an environment in which embryogenesis occurs. In the case of chickens, for instance, the optimum incubation temperature is 37.2 to 37.8° C. in a three-dimensional incubator (38.9 to 39.4° C. at the top of an egg in a planar incubator or the like), and the optimum humidity is about 40 to 70%. The environment to be employed is not limited to these, however. During the incubation, eggs should be turned. The egg turning is preferably carried out at an angle of at least 30° at least twice a day. The conditions are not restricted to these, however.

The infection of avian embryos with the virus is preferably accomplished by microinjection, which allows introduction of the virus solution into a specific site, such as heart or a blood vessel. Microinjection is a technique to introduce a virus solution directly into a specific site using a tool, such as a tapered glass microtube, under a microscope.

Preferably, sorting of transgenic birds based on expression levels of the suitable foreign protein in their blood is carried out before they reach sexual maturity.

G0 transgenic chimeric birds can be produced by infecting avian embryos with the replication defective retroviral vector containing the foreign gene that can be expressed by the endoplasmic reticulum chaperone promoter, and hatching the embryos. G1 transgenic birds can be produced by crossing G0 transgenic chimeric birds containing a foreign gene in germ cells with wild-type birds or G0 transgenic chimeric birds, and sorting hatched chicks.

The possibility that the foreign gene is introduced in all the cells of a G0 transgenic bird is very low, and most G0 transgenic birds contain cells different in genotype. In other words, cells with the foreign gene and wild-type cells without the foreign gene. G0 transgenic chimeric birds, among the transgenic birds, contain the foreign gene in cells that form the oviduct. On the other hand, G1 transgenic birds contain the foreign gene in all the cells.

In order to check that the foreign gene is successfully introduced into somatic cells or germ cells, DNA or RNA samples taken from blood, somatic cells, or spermatozoa are examined by techniques such as PCR. The expression level of the desired protein can be assayed by analyzing plasma or homogenates of organs by techniques, such as ELISA, electrophoresis, western blot, and the measurement of the activity of the desired protein.

Transgenic birds of G2 and later generations can be produced by crossing G1 transgenic birds with wild-type birds, G0 transgenic chimeric birds, or G1 transgenic birds. Crossing between a G1 transgenic cockerel and a G1 transgenic hen is preferred for efficiency reasons.

The present invention also relates to a method for producing a suitable foreign protein which includes the step of recovering the suitable foreign protein from a transgenic bird. The suitable foreign protein can be recovered from transgenic birds, specifically from blood, somatic cells, and/or eggs of transgenic birds by performing one or a combination of extraction, purification and activation of the target protein. The extraction and purification can be accomplished by any methods without limitation, and specifically accomplished by one or a combination of fractional precipitation, centrifugation, separation into two phases, ultrafiltration, membrane separation, chromatography, immunochemical methods, and crystallization, for example.

The ratio (expression level in blood)/(expression level in egg white) of the foreign protein is preferably not less than 1/1000, more preferably not less than 1/500, and most preferably not less than 1/120 for productivity reasons. In order to sort out individuals expressing the foreign protein without a burden on the hosts, the ratio is preferably not more than 1/6, more preferably not more than 1/15, and most preferably not more than 1/31.

The expression level of the foreign protein in blood is preferably not less than 700 pg/ml. This is a range that allows detection of the foreign protein in blood. The level is most preferably not less than 0.3 μg/ml. In order to reduce the burden on the hosts, the level is preferably not more than 10 μg/ml, more preferably not more than 7 μg/ml, and most preferably not more than 3.7 μg/ml.

The expression level of the foreign protein in egg white is not particularly limited, and is typically not more than 1 mg/ml.

As demonstrated in examples below, the present inventors succeeded in producing transgenic chickens expressing feline-derived erythropoietin using endoplasmic reticulum chaperone protein promoters. Detailed studies on the transgenic chickens revealed that blood sampled from chicks within one month from hatch contained feline-derived erythropoietin at 1.5 μg/ml, and namely, the expression in blood was reduced to 1/10 or lower of the expression levels in blood of transgenic chickens expressing the protein with an actin promoter (JP 2007-89578 A). It was also confirmed that the protein was produced in egg white at a level of 193 μg/ml, and this level is equivalent to the expression levels achieved by an ovalbumin promoter (Proc. Natl. Acad. Sci. USA; 104, 2007, 1771-1776) or an actin promoter (JP 2007-89578 A). Another finding is that the expression levels in blood somewhat correlate with the expression levels in egg white. This suggests that the expression levels in egg white can be predicted before sexual maturity by measuring the expression levels in blood. The term "sexual maturity" herein means that an animal grows to be able to reproduce. Chickens, for instance, reach sexual maturity at about 6 months of age to begin to lay eggs.

The following examples are given to illustrate the present invention in more detail, and are not to be construed as limiting the present invention. Unless otherwise specifically described, gene manipulation processes were carried out according to the typical methods (J. Sambrook, E. F. Fritsch, T. Maniatis; Molecular Cloning, A Laboratory Manual, 2nd Ed., Cold Spring Harbor Laboratory). Unless otherwise specifically described, cell culture processes were carried out according to the typical methods (Hideki Koyama (ed.): "Saibo-Baiyo Labo Manual (Cell Culture Labo Manual)", Springer Verlag Tokyo, 1st Ed.). Products with a trade name were used according to the manufacturer's instructions, unless otherwise specifically described. Transgenic chickens expressing feline EPO with an actin promoter were produced according to the method described in JP 2007-89578 A.

Example 1

(Step 1) Production of a Vector Construct Expressing Feline Erythropoietin Gene with a GRP 78 Promoter A blood sample was taken from the wing vein of a white leghorn chicken, and the genome was obtained using MagExtractor Genome (TOYOBO CO., LTD.). In order to amplify the GRP 78 promoter region by PCR, PCR was performed using synthetic primers for amplifying the GRP 78 promoter (dnaK3KD: 5'-ATTGAATTCACACGGAACCCGTAAACCCG-3' (SEQ ID No:3 in the sequence listing) and dnaK3KR: 5'-ATTGGATCCTCGCCGCTCTGCCAAAAGA-3' (SEQ ID No:4 in the sequence listing)), the prepared genome as a template, and a PCR enzyme KOD FX (TOYOBO CO., LTD.). The amplified approximately 3.4 kb fragment was cleaved with EcoRI (Takara Bio, Inc.) and BamHI (Takara Bio, Inc.). As a vector construct into which the promoter was to be introduced, pMSCVneobactfEPOwpre (which is a vector construct disclosed in JP 2007-89578 A) was used. This vector construct was cleaved with EcoRI and BamHI to remove its actin promoter region, and the fragment which had been amplified by PCR and cleaved with the restriction enzymes was inserted into this site. Thus, pMSCVneoGRPfEPOwpre was prepared. The sequence of the DNA cloned by PCR was determined. The determined DNA sequence is shown as SEQ ID No:1 in the sequence listing.

(Step 2) Production of Vector Construct Expressing Feline Erythropoietin Gene with PDI Promoter In order to amplify the PDI promoter region by PCR, PCR was performed using synthetic primers for amplifying the PDI promoter (PDI3-5KD: 5'-AATGAATTCCCAGGCCAGACCCCATAAC-3' (SEQ ID No:5 in the sequence listing) and PDI3-5KR: 5'-AATATCGATGAGAGCTGCGCTCCCTCTTCG-3' (SEQ ID No:6 in the sequence listing)), the white leghorn genome obtained as described above as a template, and KOD FX (TOYOBO CO., LTD.). The amplified approximately 3.5 kb fragment was cleaved with EcoRI (Takara Bio, Inc.) and ClaI (Takara Bio, Inc.), and inserted into the EcoRI/ClaI site of pBluescriptKS− (Stratagene). Thus, pBluPDI was obtained. This vector construct pBluPDI was cleaved with EcoRI and SalI (Takara Bio, Inc.), and an approximately 3.5 kb fragment was purified. As a vector construct into which the PDI promoter was to be introduced, pMSCVneobactfEPOwpre was used. This vector construct was cleaved with EcoRI and XhoI to remove its actin promoter site, and the 3.5 kb fragment cleaved with EcoRI and SalI was inserted to this site. Thus, pMSCVneoPDIfEPOwpre was prepared. The sequence of the DNA cloned by PCR was determined. The determined DNA sequence is shown as SEQ ID No:2 in the sequence listing.

(Step 3) Preparation of Retroviral Vector Using pMSCVneoGRPfEPOwpre, pMSCVneoPDIfEPOwpre, and pVSV-G Hereinafter, unless otherwise specified, Dulbecco's Modified Eagle Medium (DMEM) (Gibco) containing 10% fetal bovine serum (FBS) and 50 units/ml penicillin-streptomycin was used. Cell culture processes were performed at 37° C. in the presence of 5% $CO_2$. Endo Free Plasmid Maxi Kit (QIAGEN) was used to purify vector constructs to be used for retroviral vector preparation.

A retroviral vector containing pMSCVneoGRPfEPOwpre was prepared as follows. In order to prepare a retroviral vector using the vector construct pMSCVneoGRPfEPOwpre constructed in Step 1, a collagen-coated culture dish having a diameter of 100 mm was inoculated with GP293 packaging cells having the gag and pol genes ($5\times10^6$ cells/dish; 70% confluent). On the next day, the medium was replaced with fresh medium (7.2 ml). A 56 μl portion of Lipofectamine 2000 (Invitrogen) was suspended in 1.4 ml of Opti-MEMI medium (Gibco), and the suspension was allowed to stand at room temperature for 5 minutes. Separately, 12 μg of pMSCVneoGRPfEPOwpre and 12 μg of pVSV-G were suspended in 1.4 ml of Opti-MEMI medium. The Lipofectamine 2000 solution and the DNA solution were mixed, and the mixture was allowed to stand at room temperature for 20 minutes. The whole amount of the resulting mixture was added to the culture dish, the medium of which had been replaced with fresh medium, and cultivation was carried out for 6 hours. After the cultivation, the medium was replaced with fresh medium (8 ml), followed by further cultivation for 24 hours.

The culture supernatant was collected in a centrifuge tube through a 0.45-μm cellulose acetate filter (Advantec). The filtrate was centrifuged at 28,000 rpm (5,000 g) for 1.5 hours using an ultracentrifuge CS100GXL (Hitachi Koki). The supernatant was removed, and the sediment was combined with 20 μl of TNE buffer (50 mM Tris-HCl (pH 7.8), 130 mM NaCl, 1 mM EDTA), and suspended well. The suspension was centrifuged at 12,000 rpm for 1 minute using a small-sized high-speed centrifuge, and the supernatant was passed through a 0.45-μm Durapore Ultra-Free filter (Advantec) to give a virus solution.

A retroviral vector containing pMSCVneoPDIfEPOwpre was likewise prepared according to the above processes.

(Step 4) Measurement of Virus Titer

The titer of the virus solutions was determined by adding each virus solution to NIH3T3 cells (American Type Culture Collection CRL-1658), and counting infected cells. Specifically, the titer of each virus solution was determined as follows: diluting a 1 μl portion of the virus solution in 2 ml of the medium; further diluting this dilution to concentrations of $10^1$ to $10^5$; charging the resulting dilutions to 6-well culture plates, each well of which contained $1.5\times10^4$ NIH3T3 cells; and determining the proportion of cells expressing the neomycin resistance gene, which is a marker gene, based on the resistance against G418. In the case of one colony at $\times10^5$ dilution, the virus titer is: $1\times10^5$ cfu/2 ml×2000=$1\times10^8$ cfu/ml.

Specifically, one day before the titer measurement, NIH3T3 cells were inoculated into 6-well culture plates at $1.5\times10^4$ cells/well, and cultured. On the next day, a 1 μl portion of each virus solution was suspended in a medium containing 2 ml of polybrene (final concentration: 8 μg/ml). The virus dilutions were further diluted in the polybrene-containing medium to concentrations of $10^1$ to $10^5$, and the media of the cell cultures were replaced with these virus dilutions. In this manner, NIH3T3 cells were infected with the viruses. One day after the infection, the media were replaced with a medium containing 1 mg/ml of G418 (Sigma). Thereafter, the media were replaced with the G418-containing medium every other day for one week. After one week, the plates were dyed with a 0.5% solution of Crystal violet (NACALAI TESQUE, INC.) in ethanol, and colonies were counted to determine the titer.

(Step 5) Sorting of Stable Packaging Cell

On the day before viral infection, 24-well culture plates were inoculated with $1\times10^4$ GP293 cells per well, and the cells were cultured. On the day of viral infection, the medium was replaced with 1 ml of a medium containing 8 μg/ml of polybrene, followed by infection with the virus solutions prepared in Step 3. Thereafter, cells were cloned by limiting dilution. Specifically, on the next day, cells were treated with trypsin, and the cell suspensions were diluted in a medium containing 1 mg/ml of G418 to 13.3 cells/ml.

Each dilution was distributed in 150 μl portions into the wells of a 96-well culture plate, followed by cultivation for 1 to 2 weeks. One colony was grown per well. Cell lines showing a high cell growth rate was selected and, thus, stable packaging cell clones were obtained.

(Step 6) Preparation of Retroviral Vector Using Stable Packaging Cells Containing pVSV-G Collagen-coated culture dishes having a diameter of 100 mm were inoculated with the stable packaging cells obtained in Step 5 (6 to $7\times10^6$ cells). On the next day, the medium was replaced with fresh medium (7.2 ml). A 56 μl portion of Lipofectamine 2000 was suspended in 1.4 ml of Opti-MEMI medium, and the suspension was allowed to stand at room temperature for 5 minutes. Separately, 24 μg of pVSV-G was suspended in 1.4 ml of Opti-MEMI medium. The Lipofectamine 2000 solution and the DNA solution were mixed, and the mixture was allowed to stand at room temperature for 20 minutes. The whole amount of the resulting mixture was added to each culture, followed by cultivation for 6 hours. After the 6-hour cultivation, the medium was replaced with fresh medium (8 ml), followed by cultivation for 48 hours. The supernatant of each culture was passed through a 0.45-μm cellulose acetate filter and collected in a centrifuge tube. The filtrate was centrifuged at 28,000 rpm (5,000 g) for 1.5 hours using an ultracentrifuge CS100GXL. The supernatant was removed, and the sediment was combined with 20 μl of TNE buffer solution, and suspended well. The suspension was centrifuged at 12,000 rpm for 1 minute using a small-sized high-speed centrifuge, and the supernatant was passed through a 0.45-μm Durapore Ultra-Free filter to give a virus solution. The virus solutions thus obtained had a titer of not lower than $1\times10^8$ cfu/ml.

(Step 7) Microinjection of Retroviral Vector into Chicken Embryo and Artificial Hatching Microinjection and artificial hatching were carried out under sterile conditions. Fertilized chicken eggs (Shiroyama Shukeijo (Shiroyama Chicken Farm)) were externally disinfected with a disinfectant (Showa Furanki) and 70% ethanol. The eggs were incubated in an incubator (model: P-008(B), Showa Furanki) which was adjusted at 38° C. and a humidity of 50 to 60%. The incubation was started by turning on the power to the incubator, and the eggs were turned at 90° at 15-minute intervals.

After the lapse of about 55 hours from the start of incubation, the eggs were taken out of the incubator, and an approximately 1 mm hole was made on the blunt end of each egg. Then another hole with a diameter of about 7-10 mm was made slightly above the center of the lateral side of each egg. The virus solutions prepared in Step 6 were charged to Femtochip II (Eppendorf), and approximately 2 μl portions of the virus solutions were injected into the heart of chicken embryos from the 7 to 10 mm hole using Femtojet (Eppendorf) under observation by a stereo microscope system SZX12 (Olympus Corporation).

After the injection with the virus solutions, the holes were sealed with Scotch Tape BK-15 (Sumitomo 3M Limited), and the eggs were returned to the incubator for continued incubation. The mode of egg turning was changed to 30° turning at 30-minute intervals. One week after the start of incubation, oxygen was fed to the incubator at 60 cc/min to hatch eggs. Egg turning was stopped on day 19 from the start of incubation to allow chicks to naturally hatch.

Comparative Example 1

Production of Transgenic Chicken Expressing Feline EPO with Actin Promoter

Transgenic chickens expressing feline EPO with an actin promoter were produced in the same manner as in Steps 3 to 7 of Example 1, except that pMSCVneobactfEPOwpre (JP 2007-89578 A) was used.

(Measurement 1) Confirmation of Expression of Feline-Derived Erythropoietin in Blood and Egg White of Transgenic Chicken Expressing the Protein Chicks hatched in Step 7 of Example 1 were reared. The feeds used were SX Safety for young chicks and Neo-Safety 17 (products of Toyohashi Shiryo (Toyohashi Feedstuff)). Blood samples were collected from the wind vein of the transgenic chickens. The collected blood samples were transferred into Eppendorf tubes and, after at least 30 minutes of standing at room temperature, centrifuged at 3,000 rpm at 4° C. for 5 minutes using a small-sized high-speed centrifuge to completely separate into serum and blood clot. The supernatant was used as serum. Egg white was made entirely homogeneous with ultrasonic waves.

The feline-derived erythropoietin activity was determined by the cell proliferation assay technique using the EPO-dependent cell line BaF/EPOR (JP H10-94393 A). In the cell proliferation assay, a standard curve for proliferation was constructed using Epogin (Chugai Pharmaceutical) as a standard erythropoietin, and the erythropoietin activity of unknown samples was determined based on the standard curve for proliferation. The medium for culturing BaF/EPOR cells used was RPMI 1640 liquid medium (Nissui) containing 5% fetal bovine serum (FBS) and 50 units/ml penicillin-streptomycin. In the normal BaF/EPOR cell culture, Epogin was added to a final concentration of 1 U/ml. In the cell proliferation assay, cells at the logarithmic growth phase were used.

Before the cell proliferation assay using BaF/EPOR cells, the Epogin in the medium was removed. Specifically, a 10 ml portion of the cultured BaF/EPOR cells was centrifuged at 1,000 rpm for 5 minutes. The supernatant was removed, and the sediment was combined with 10 ml of the Epogin-free medium, and suspended. The Epogin in the medium was removed by repeating the above procedure three times. Cells were counted and diluted in the Epogin-free medium to a concentration of 55,555 cells/ml. The diluted cell suspension was distributed in 90 μl portions into the wells of 96-well microtiter plates. Thereto were added 10 μl each of Epogin solutions diluted to 25, 16, 10, 6.4, 4.0, 2.5, 1.6 and 1.0 U/ml, and the cells were homogeneously suspended therein (the final Epogin concentrations being 2.5, 1.6, 1.0, 0.64, 0.4, 0.25, 0.16 and 0.1 U/ml, respectively). Samples to be assayed were diluted serially 10-fold in the medium to prepare samples with concentrations within the assay range of the standard curve. A 10 μl of each dilution was added to the inoculated cells, and the cells were homogeneously suspended. Each of the standard samples and unknown samples was measured at three different points. After two days of cultivation, 10 μl of the solution included in Cell Counting Kit-8 (Dojindo Laboratories) was added to each well. After allowing the color reaction to proceed from 1 to 4 hours, 10 μl of 0.1 mol/l hydrochloric acid was added to terminate the reaction, and the absorbance at 450 nm was measured using a microplate reader. An approximate expression was determined from the measurement results of the standard samples by logarithmic approximation, and the activity of each unknown sample was calculated based on the approximate expression obtained. The feline EPO protein weight was calculated as 130000 IU=1 mg.

The transgenic chickens expressing feline EPO with the endoplasmic reticulum chaperone promoters obtained in the example were measured for the feline EPO levels in blood and egg white. Table 1 shows the results.

TABLE 1

| No | Promoter | Sex | Expression level in blood (μg/ml) | Expression level in egg white (μg/ml) |
|---|---|---|---|---|
| GE1 | GRP | ♀ | 1.6 | 193 |
| GE2 | GRP | ♀ | 2.0 | 86 |
| GE3 | GRP | ♂ | <0.1 | — |
| GE4 | GRP | ♂ | 0.7 | — |
| GE5 | GRP | ♀ | 1.4 | 53 |
| GE6 | GRP | ♀ | <0.1 | 5 |
| GE7 | GRP | ♀ | 1.0 | 71 |
| GE8 | GRP | ♂ | 0.3 | — |
| GE9 | GRP | ♂ | 1.1 | — |
| GE10 | GRP | ♂ | 2.1 | — |
| GE11 | GRP | ♂ | 1.2 | — |
| GE12 | GRP | ♀ | 0.9 | 31 |
| PE1 | PDI | ♀ | 0.8 | 25 |
| PE2 | PDI | ♂ | 0.6 | — |
| PE3 | PDI | ♂ | 3.7 | — |
| PE4 | PDI | ♂ | 0.6 | — |
| PE5 | PDI | ♀ | 1.4 | 46 |

In order to measure the feline EPO levels in blood and egg white of the transgenic chickens expressing feline EPO with the actin promoter, the same procedures as described above were performed except that the transgenic chickens of the comparative example were measured. Table 2 shows the results.

TABLE 2

| No | Promoter | Sex | Expression level in blood (μg/ml) | Expression level in egg white (μg/ml) |
|---|---|---|---|---|
| AE1 | Actin | ♀ | 21.9 | 110 |
| AE2 | Actin | ♀ | 1.6 | 0 |
| AE3 | Actin | ♀ | 27.0 | 47 |
| AE4 | Actin | ♂ | 31.0 | — |
| AE5 | Actin | ♂ | 27.1 | — |
| AE6 | Actin | ♂ | 21.8 | — |
| AE7 | Actin | ♀ | 8.1 | 47 |
| AE8 | Actin | ♂ | 2.5 | — |
| AE9 | Actin | ♀ | 0.2 | 0 |
| AE10 | Actin | ♀ | 11.5 | 20 |

As seen in Tables 1 and 2, the expression levels of feline EPO in blood by the endoplasmic reticulum chaperone promoters were less than about 1/10 of the levels of expression by the actin promoter; while the expression levels of feline EPO in egg white of the transgenic chickens expressing feline EPO with the endoplasmic reticulum chaperone promoters was equivalent to or higher than those of the transgenic chicken expressing feline EPO with the actin promoter.

(Measurement 2) Measurement of Survival of Produced Transgenic Chickens Until Sexual Maturity Transgenic chickens expressing feline EPO with the endoplasmic reticulum chaperone promoters which were hatched in the manner described in steps 1 to 7 of Example 1 and transgenic chickens expressing feline EPO with the actin promoter which were hatched in the manner described in Comparative Example 1 were reared for six months from hatch, and chickens that died in this period were counted to determine the survival. Table 3 shows the result of the survival until sexual maturity.

TABLE 3

| Promoter | Survival (%) |
|---|---|
| GRP promoter | 100 |
| PDI promoter | 100 |
| Actin promoter | 83 |

As seen in Table 3, the survival until sexual maturity was 100% for the endoplasmic reticulum chaperone promoters, whereas the survival was as low as 83% for the actin promoter. This demonstrates that expression of feline EPO throughout the body decreases the survival.

INDUSTRIAL APPLICABILITY

The present invention enables a suitable foreign protein to be expressed in the egg white of transgenic birds at levels equivalent to or higher than those of transgenic birds expressing the suitable foreign protein with an ovalbumin promoter or an actin promoter, and reduces the expression at sites other than the oviduct to reduce the great burden on birds but achieves expression sufficient to predict the expression levels in egg white before the birds reach the sexual maturity. Thus, the present invention provides very suitable transgenic birds for the industry, compared to the conventional techniques.

The invention claimed is:

1. A transgenic chicken, comprising an exogenous nucleic acid sequence encoding an exogenous protein operably linked to an avian endoplasmic reticulum (ER) chaperone promoter comprising the nucleic acid sequence of SEQ ID NO: 7, wherein the transgenic chicken produces the exogenous protein in its eggs and/or blood.

2. The transgenic chicken according to claim 1, wherein the avian ER chaperone promoter is from a chicken.

3. The transgenic chicken according to claim 1, wherein the avian ER chaperone promoter is a glucose-regulated protein 78 promoter or a protein disulfide isomerase promoter.

4. The transgenic chicken according to claim 3, which comprises a glucose-regulated protein 78 promoter as set forth in SEQ ID NO: 3.

5. The transgenic chicken according to claim 3, which comprises a protein disulfide isomerase promoter as set forth in SEQ ID NO: 5.

6. The transgenic chicken according to claim 1, wherein the exogenous protein is a feline-derived protein.

7. A method for producing an exogenous protein, comprising the step of recovering the exogenous protein from the transgenic chicken according to claim 1.

8. A method for producing a transgenic chicken, comprising the step of introducing an exogenous nucleic acid sequence into a chicken wherein the exogenous nucleic acid sequence encodes an exogenous protein operably linked to an avian endoplasmic reticulum (ER) chaperone promoter comprising the nucleic acid sequence of SEQ ID NO: 7, and wherein the transgenic chicken produces the exogenous protein in its eggs and/or blood.

9. The method for producing a transgenic chicken according to claim 8, further comprising the step of sorting the transgenic chicken based on expression levels of the exogenous protein in blood before sexual maturity.

* * * * *

SEQUENCE LISTING

```
<160> NUMBER OF SEQ ID NOS: 7

<210> SEQ ID NO 1
<211> LENGTH: 3377
<212> TYPE: DNA
<213> ORGANISM: Gallus gallus

<400> SEQUENCE: 1

acacggaacc cgtaaacccg gcggtcccgg cgctcgcgcc gctccgcagc cacgcatggc      60

gccgtcccgc cgcagcagag agcgcgaagg gccgcagccg cgaagcgctc ctgatcggcg     120
```

-continued

```
accaccgccg cgaagcccgg cgctaacatg gcagcggggc cgcgggcagc aggcggagcg    180
cggcccggtc agctcccacg gcgcggactg cgagcgcggc ccccgcccgg cgctgggagc    240
ctccccccgc ccggggaacg cagacgagat cggcacctcg gtgtgtcggc ctgctcctcg    300
cagcgctgcg agccgcgctt cccactcggc tccctgaaaa agcagagagg ggttggtcag    360
gcccgggccc cgctctcctt tccttcccct cccctccgct cccttccccc gcaccgccgg    420
agaggggggg gaatccgagc ggcggtcccg gccgcgcggg ctgcgagctc tcccctaccc    480
ggccccggct ccgccgccgc ccggctctgc tgcggccccg agccaggcgc ggcgcggcac    540
tgcgcaggcg gcgggcggcg acgccgcgct cctgggacat gtagtcccgc ggccatgcag    600
tcccgcgggc acggagcccc ggcccgggtt ctttcttcag cccccaccga ggctgcgttt    660
cggcggagca tctccgatgt ggggctgctg ctgggtggcg cggggaaaaa tcgggctcgg    720
agcggtcact tcacgctgcg tggcactgat gggcaccgtt ccctgggatg catccagacg    780
gacgctgccc ttctcccgca gctgctttac aaggaagggc tcggccagcc ctgcggatgg    840
aaacgcacgg tgacaaatag agtatggaac gtgtaacagc gctgcgtgga gcaatctgcc    900
tcacgtaata gcactgctta atcataacca gcatcacatg cgactgcaca atcaaaggtg    960
attactgctt gatggtcaca gactgatttt aactttgccc tcctttttca gctatcccaa   1020
gatcctcaga aagcacagag ctcgctgtct gcccacagga tggggccttg cacagcttca   1080
ccatggcaag caggcggctg agatcggaca gctgcacgca cagctacagc ccaaacccac   1140
ccccacccac cccatccagc gctcctcata acacgagtag ctcaaataga aatatcaggg   1200
aaatctatgt cttaggacat aatttattac acaaaaaact gccccaacag aggtattaag   1260
aagcttgttc tcttatagag aaaaagtata attggagaca ccatttgcag cccagctctc   1320
acttgggcac cttgttacag tgtgcaatgg cagcagtaag ccaagaccca gcacgctgtg   1380
gtcagggcat ggcatccagg ctgcagcgtg gggcagcggt gacttgggtg ggaaagtaac   1440
actcctcagt caccatcatg gcttcttcgt gcctaagcca tctgcagagc tcttctcagt   1500
gtcagctcag cacagcagcc acccatcagt gctttgtctc tctcaatctc caaactatta   1560
tgtgtgctct tttcttagct gacagttaca gcctcaaatc cacttctctg ataaaacaga   1620
atgccttaca taattgaatt ttaaatatct aaatgatgtt taagaaacaa ccacggcaca   1680
cagaaatgta acaacaaaac aaagtccctt aagcccaaac acacaccagc aaaccactac   1740
gtctgtgcaa cacagccagc tgccacactg tgttcctggc tgtaacgcag aacaccggct   1800
gtactaagca tcactgccct tagagaactg aggggaatga gcctgaggcc tggaagcatc   1860
aaaatgtccc cttgtctgca catggtttcc cgtgaaaaga taaaatatgg tacgcgcagc   1920
tctcaggaca cgcagctgta gcaaagacag ttattttcta aggctaagct cagtaatttg   1980
catcaggatt cttcaaatat gtgaattaaa tgcagaaata actgactaaa agaaataaat   2040
tgcacaatga catatagagg attctgaaac atactaaaga ataggaagac agcatccaga   2100
ttaaaacagc ttttgaagag gtgtagtggg aacagcgcgg ttacagctgt gctcccctcg   2160
gggcagtgac ccacccaggc tgtggggcct cccagcacag ggcagcaccg aggctccctt   2220
ctgacggcgc gcagctcaag gctctccctg gagccacact tttatacaac ctggaattat   2280
ttttgctacg attcagccct gttatcaccc agaagttaac aactccaatt ttctcatgtc   2340
actcttgacc aacccaaggc actcatttct ctacatcgga gctctgcagc tgtcagcacg   2400
cagacacgac cccaggcccc ggagctgcgg ccctgctggc tgtgggacag ccccggggct   2460
```

```
gatgtaactc agcgcaacat cggggcgagg gtgcggtgag tcggtgtcca ggcacagctg   2520

cctgcagggc cggggccccg tgcccatagg ctgcgtgcca agcacggcgc tcctggcaca   2580

gacagccccg accaggcccc gacccgagcg ctgcggggct gcacggagcc cgcacatcac   2640

gcggggcccc gcggctccac agggacgatg cggaccccgg ggcacggccc tctggcctga   2700

ccagcccggg tgcggccctc cttcttccgc ctgggtctcc gcggcctcct cggtctctgc   2760

tgcgctcggc cgagagggtg caccgtcacc gggacccctc cgcagcaccg gggttggtta   2820

ccatggaaac ttccagaacg tcgtcccgtc ccccccaccc tggcctcgcc accacggccg   2880

cccccaacca atgagcttct tccgcttggc tcacgcttct ctgttgattg gcccgcgacg   2940

ccggcggggt gaaccaatcg cgtggcagaa gggggtgcgc gccaggcatg tcagagcgac   3000

cgcccgctcc tcgccaatca agggaggcca gcttagtagc agacgggcca atgagcgcac   3060

tccagctagg gctctgcggg ccaatggcga gcctccacga aggagtaacg aaggatatat   3120

aagggcgggc ggcgcggcct gggtgttcag cggcagttgg agacgcgacg gttcgtgtgt   3180

gacggtaggg gcggtggtgg ggcctattgc ggcctgcagg gaccggtggg gcctgggggt   3240

tggcggtttt ggggtgtctg cgagagggga ctgggcgcgg tgggggaggg gagggcgggg   3300

gcgatgaggt cgggttggac cgtgccgccc atgtggtgcc tccattttgt gaccggcgtc   3360

ttttggcaga gcggcga                                                  3377
```

```
<210> SEQ ID NO 2
<211> LENGTH: 3533
<212> TYPE: DNA
<213> ORGANISM: Gallus gallus

<400> SEQUENCE: 2

ccaggccaga ccccataaac atgtgctgct gtagccttgg ctctctctgc tccttacccc     60

acctggccct gtgcccgcag agaggcacac agatgggtct tgatatcctt gagtagctct    120

ccctggatgt ccccaggcca ctgcttccct gagggaatgg gcctgaggag tcccaggggc    180

tgcatgtggc tgtggggcgg gaagcctggg ggcagccagc agcagggtgc ctggagctgc    240

tgggacagga ggggcttggg aaagtgttcc tggcattgct gcaggcatgc agggagcagg    300

gctagatgcc catcaccagt ttcctggggg atgctcacag caagccatgg gcaggcagag    360

gagagccaaa gtagggtctg gctctgtctc tctttctgcc tgcaggaaag aaagcaccat    420

cagagcacgg catgccaacc tggtgctcca tgggaagggc tcgtgtcctc actgctgctg    480

ggagcccttc acagtgctca ctcacacgtt cacatatata cgcatacacg cgcagctctg    540

ctcaggaata gcacagtgct gctgtcccca gagctgctat tcgaggccgg gttttgggca    600

ggaggcagca gaaaggagct cctgctgggc acggcccgag gagcagcacg agccgggcag    660

cggggccagg cgtcagccgt tcccttgcaa acctgcgcgg tgtgacccgg cgagctgccg    720

agctcccagc tgtcccggtc ccgtatcccg gtcccgcaga gcagccgtcc cagcaccacc    780

agcaggcggc tcccggtccc gcagccccgg ctctcccagc tcggtgcccg ggcggcccaa    840

gcgcggggtc cgaggcagcc gcagcacagc ggcacccggg agggtggttg gcacggcgca    900

gcccccgcgg gaccgcaccc cgcacagatc ccccgcgtgg gacaacatct caaaagctac    960

cgcagctccc cacgccccgc ccagcagacg cctctcggca cggccccacg ttccctccac   1020

cgtccgggcc cagcccaggg cagccggctg ccggtcggtg cgcagcgccg ggtcccggct   1080
```

```
caacccccgg gcacccctcc gtcgcgggta ggttgagccc ggccgtgccc cgcgcacccc   1140
gcccgccgct accggggagt cccgcagcgc cctctgccgg ccccggggcg gcgcggagca   1200
acgggtccgg gagtaacgga gtgacggcgg agcgagccgc ggcccggcag cctcggttat   1260
ctgaaggcgg cgggtgggag gaaggcgtcc tccttttgag cagagcctgg tgctgctgct   1320
cggacagagc agcgcccttc gagatgtcca gggattacgg gggggtcagt ggctgagtct   1380
ggcccagcag tcagcagtga tggctgcgac aacattctgc aagaggaaag acccaatcag   1440
tatccagacc acagcgtggg ttccactgat gatcttgttt atagtgggag tcttccggat   1500
gtcctggagc agtctaagcc actcatccag gctgaagaga ataaagacag cccgcagagc   1560
acgggaaagc tactgcaaga agaaaatggc tctgtcatgt gaggcatctg tggcagttgc   1620
tcagacagct gtcagctggg tttctccctg cctggttaca gggtgagcac aggaggatgc   1680
ctgcccgaga gaaacaagtg gggaggcaga aacgctggtg cttagaactg tcccaccaag   1740
tccagcagag atgccggacc ggctgtggca gagggcagca cgtgggggct gggaccaggg   1800
agcaaaggcc caggtttgtg gcactagttc ctgaaaaggg tgtgatggga cacatcagga   1860
agaggggctg tcgctccatg ctggctgtag ctggggaagg tggctacaga caagaacttc   1920
acatgtgctg gcactcatgg gcacgttcca caaagctacc gtgcagaggg cagaacccca   1980
ggcctgccgc cgtgctgtgc cacgaggagt gagacctctg cacagggaga gcccagctca   2040
gtgcagcagc agcactgcgg gaagggcgct gtgtgtgctc acagattttg atgatctgga   2100
ttactggtaa caggatgacc aggtggaacg tggctgttct gtacgtagaa cctgagattt   2160
gtcactgaga aaaaagcaca ggatgctgac taattgcctg acaaagtcca tggtcagatg   2220
catgcggatg ggactcagaa gaacaccaga tgcatatggc tccatggagc tcaggtttca   2280
cgacaagctt ggactttgtc tcagtacacc tccaatagag ttctgccttt gacaagggac   2340
agtcaaagca ctggaaaagc tgcaaagtgt caccagcaaa ggctgctggg cagcagctgc   2400
ccattgagaa agaatggctg gggctggag ccgagcactg atctgttctc acagtccttg   2460
ctcacccacc tccggacaaa cgctgcttct gtgcagcagg ctctgctggc ggcgcagccc   2520
aacgcaccct gggctgcagt gcaagtggtc ccacgctcac tgccgaggca gctgtgagag   2580
gacactgagc agggtccgct tatccgtggg gtgaggagag gaaagcggct ctcgtggatc   2640
ccagtgcggc tgcacgggca tttgtatgcg gagacgaagg tcttggtgcg gcgggcagca   2700
aagcagacca agtggtgttg atccctgcgc atcagctggc tctgcttctt gcagtgcgtg   2760
tagatttgaa gcagctcccg ggaggaggga gccaagcggc agaggcggca ctggacgaac   2820
tgctggccat gcagcccccc tcgagaagca cagggggcac aacaacactg cgagagaaag   2880
ccaacttgct ggacagcttg ctaggccgtc cctaaaactt cttgacggag tgtcagtgct   2940
gaggcagcgc aagcaacaac aaagagctgg gatcgggctg ggctgtgcct ccagcagccg   3000
ccccaggatc acacggcacg gctgaggaag ggaccgtgcg cgaactccag ctccagccaa   3060
ggcgctcctt gcccagctac catcatccgc tctgcgcgca gcctcaactg agcctgcgac   3120
cgcccgctga gctgggatgc gcaccagcgt gccgaaatgc tttccttcag cggcgcctgc   3180
aggggcggac gcctctgccg cccgccaagg cccgggcggg gctgggaagg ccgacagccc   3240
gctgcccgct gcccgttgct cgttgcccgt tgcccagcgc ccccacgccg ccccctcgcg   3300
```

gcccggcctg caccgggacc cagcggcccg cgggggcggg acggccgctg cagttccccg 3360
cccgccctgc tcggcagccc attggtcacg gctctcgtga cgtaatgcac ggcgcccaat 3420
ggggagctgc cacacggcag atccggctgc ggaggaggga cttccggcct gcggccccg 3480 gcgcctgttc agccgccgcc gtcgccgaag agggagcgca gctcatcgat acc 3533

<210> SEQ ID NO 3
<211> LENGTH: 29
<212> TYPE: DNA
<213> ORGANISM: Artificial Sequence
<220> FEATURE:
<223> OTHER INFORMATION: dnaK3KD

<400> SEQUENCE: 3
attgaattca cacggaaccc gtaaacccg 29

<210> SEQ ID NO 4
<211> LENGTH: 28
<212> TYPE: DNA
<213> ORGANISM: Artificial Sequence
<220> FEATURE:
<223> OTHER INFORMATION: dnaK3KR

<400> SEQUENCE: 4
attggatcct cgccgctctg ccaaaaga 28

<210> SEQ ID NO 5
<211> LENGTH: 28
<212> TYPE: DNA
<213> ORGANISM: Artificial Sequence
<220> FEATURE:
<223> OTHER INFORMATION: PDI3-5KD

<400> SEQUENCE: 5
aatgaattcc caggccagac cccataac 28

<210> SEQ ID NO 6
<211> LENGTH: 30
<212> TYPE: DNA
<213> ORGANISM: Artificial Sequence
<220> FEATURE:
<223> OTHER INFORMATION: PDI3-5KR

<400> SEQUENCE: 6
aatatcgatg agagctgcgc tccctcttcg 30

<210> SEQ ID NO 7
<211> LENGTH: 19
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (6)..(14)
<223> OTHER INFORMATION: n is a, c, g, or t

<400> SEQUENCE: 7
ccaatnnnnn nnnnccacg 19